United States Patent [19]

Kjellander et al.

[11] 4,204,045
[45] May 20, 1980

[54] DEVICE FOR EXAMINING MICROORGANISMS

[75] Inventors: Jan O. Kjellander; Dan G. Danielsson, both of Örebro, Sweden

[73] Assignee: Orion-Yhtyma Oy, Finland

[21] Appl. No.: 877,894

[22] Filed: Feb. 15, 1978

[51] Int. Cl.[2] .......................... C12M 1/20; C12Q 1/20
[52] U.S. Cl. .................................... 435/301; 206/633; 220/22; 435/33
[58] Field of Search ......... 195/127, 139, 140, 103.5 K

[56] References Cited

U.S. PATENT DOCUMENTS

| 3,234,107 | 2/1966 | Kaufman et al. | 195/139 |
| 3,713,985 | 1/1973 | Astle | 195/127 X |
| 3,728,228 | 4/1973 | Duranty | 195/127 |
| 3,902,972 | 9/1975 | Beckford | 195/139 |
| 3,912,596 | 10/1975 | Haque et al. | 195/127 |
| 4,054,490 | 10/1977 | Vesterberg | 195/127 X |

Primary Examiner—Raymond N. Jones
Assistant Examiner—Robert J. Warden
Attorney, Agent, or Firm—Stevens, Davis, Miller & Mosher

[57] ABSTRACT

A device for investigating the effect of biologically active substances on microorganisms comprises a vessel having a bottom on which there is arranged a gel layer, and from the bottom of which vessel there extend upstanding walls which delimit a plurality of mutually adjacent, elongate, rectangular compartments. To facilitate the distribution of microorganisms of the gel layer, the compartments are open at one short end thereof in a manner such that the rectangular gel fields located in respective compartments merge directly at the open end thereof with a further gel field extending along the short side of all said compartments.

1 Claim, 8 Drawing Figures

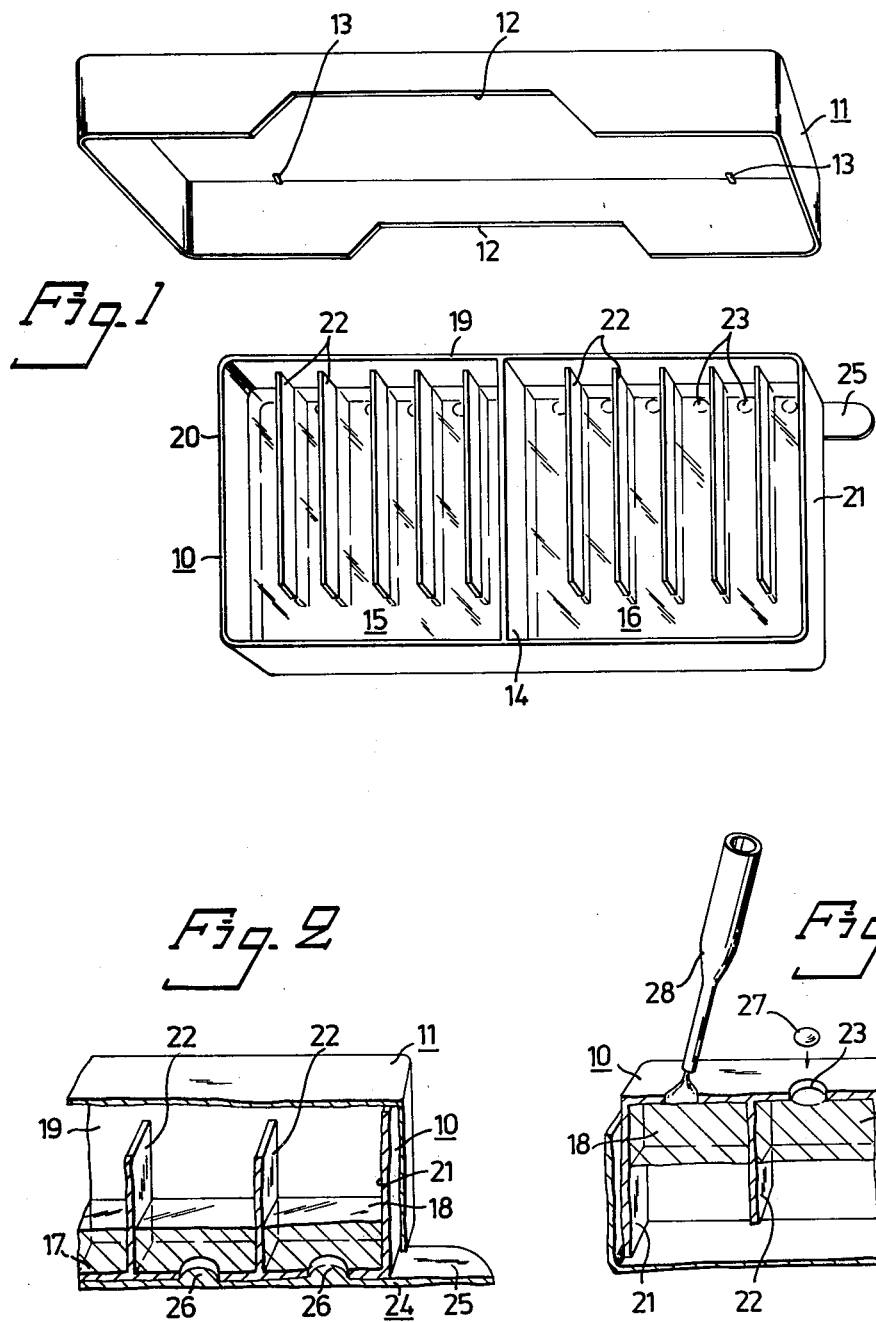

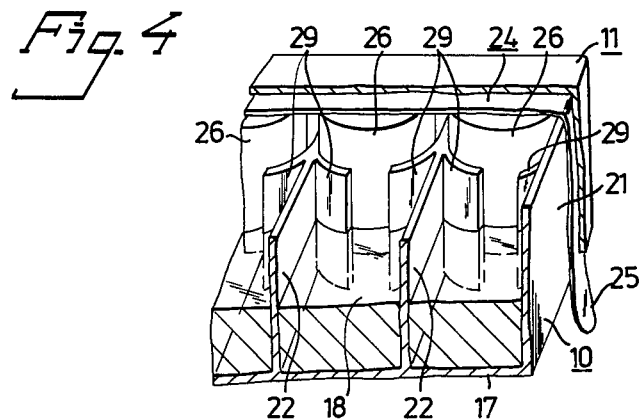
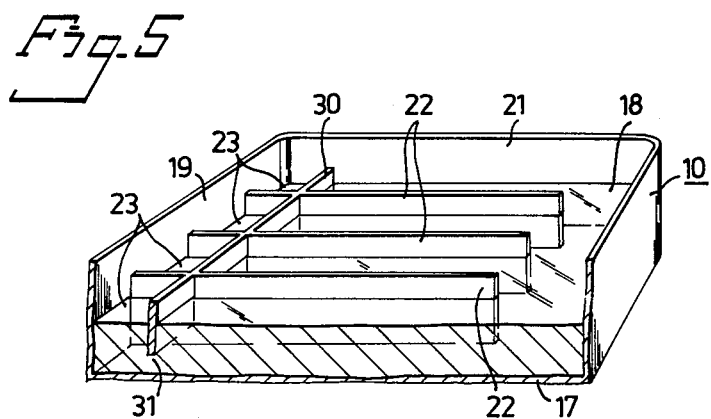
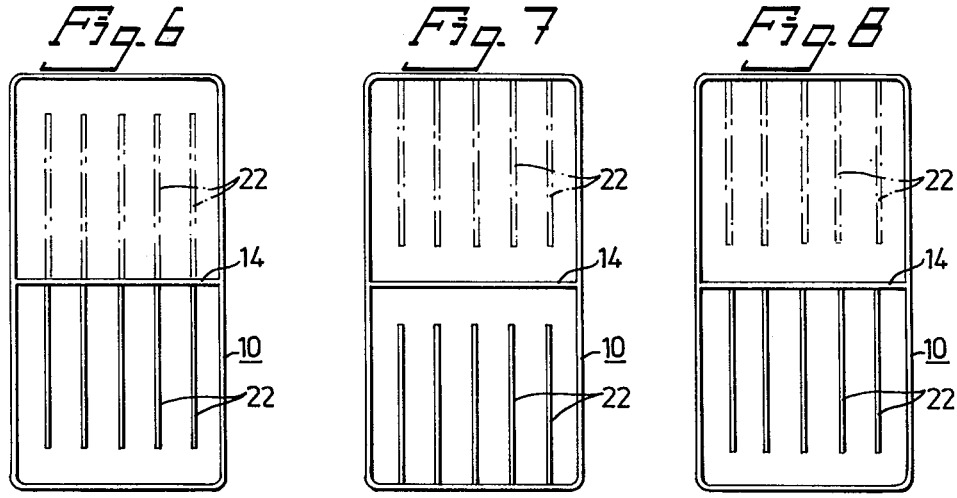

DEVICE FOR EXAMINING MICROORGANISMS

The present invention relates to a device for investigating the effect of biologically active substances on microorganisms in accordance with the diffusion method, in which the microorganisms are distributed over a gel layer on which there is also locally applied predetermined quantities of biologically active substances capable of diffusing through the layer.

By microorganisms it is meant here, in addition to bacteria, rickettsia, viruses and bacteriophages, also such fungi as mould, yeast and slime fungi, and living cells. By biologically active substances it is meant those substances which influence the metabolism in a negative or positive sense, for example promote the growth and/or the multiplication of said microorganisms, such substances being vitamins, amino acids, nutrients and other growth factors, and microorganisms having a stimulating effect on the first mentioned microorganisms, and also those substances which inhibit growth and/or multiplication of or kill said microorganisms, such as inhibitors, antibiotics, desinfecting agents and microorganisms having an antagonistic effect on said first mentioned microorganisms.

There is often the need to carry out investigations of the type recited above within the biological field and the field of medicine, and particularly within the field of microbiology. As an example of these investigations can be mentioned the isolation and classification of certain strains or mutants of microorganisms from mixtures of microorganisms, the graduation of microorganisms with respect to whether or not they are affected in a positive or negative sense and to what extent they are affected, or whether they are dependent upon different biologically active substances and the extent to which they are dependent, and concentration determinations of biologically active substances, such as the determination of the concentration of antibiotics in blood and urine samples within health services and in foodstuffs, such as milk or milk products, within the foodstuff industry.

Hitherto, the aforementioned investigations have to a large extent been carried out in accordance with the so-called diffusion methods. According to these methods, microorganisms are cultivated in round Petri-dishes on a coherent cultivating substance, normally formed by a carrier comprising agar gel and a cultivating medium comprising a suitable nutrient. Normally the biologically active substance is applied locally to the carrier in either droplet or tablet form or so-called disc-form. The commonest of the diffusion methods applied is the disc-diffusion method, which is well established worldwide, for determining the sensitivity of microorganisms to antibiotics. Small round discs, or roundels, of filter paper containing different types of antibiotics or antibiotics in different concentrations are applied to the surface of the cultivating substance subsequent to sowing the microorganisms thereon. Upon subsequent incubation, the antibiotics diffuse out into the cultivating substance in a radial direction from the location of application, and the microorganisms multiply in numbers in those regions of the cultivating substance where the concentration of antibiotics active against the microorganisms is not high enough to obstruct growth. If the antibiotic in question is active against the microorganisms, there is obtained nearest the application locations, where the concentration of antibiotics is relatively high, a zone in which there is no visible occurrence of microorganisms. The diameter or radius of this inhibiting zone is measured and, if accurate standardization measures have been taken, constitutes a measurement of the sensitivity of the microorganisms to the antibiotic in question, it being possible to express the sensitivity of the bacteria in the form of an exact inhibiting value, so called MIC-value, or, which is normally the case, in a semi-quantitative term, so-called sensitivity group.

One disadvantage with the above recited diffusion methods for determining the resistance to antibiotics is, however, that the diffusion takes place freely in all planes so that circular zones are obtained. This means that the method requires substantial space. A Petri-dish having a diameter of 9 cm will normally accommodate at most five application locations. If more application locations are required, for example due to the fact that more antibiotics shall be tested, which is normally the case, the dish must be correspondingly larger.

In order to reduce the space required to carry out the investigations, it has been proposed to divide the gel plate, by means of partitions, into discrete, elongate, relatively narrow rectangular compartments, diffusion being permitted to take place substantially only in the longitudinal direction of a compartment. The problem with this method, however, is that it is difficult to sow the gel surfaces in each compartment uniformly with those microorganisms to be investigated, and the removal of any surplus inocculate, for example urine, is a time-consuming task. Furthermore, the process steps, which are more complicated than those carried out with Petri-dishes, render personnel carrying out said process steps more liable to infection.

The object of the present invention is to provide a novel and useful device for investigating the effect of biologically active substances on microorganisms, said device at least substantially eliminating the aforementioned disadvantages.

In accordance with the invention there is proposed to achieve this end a device of the type comprising a vessel having a bottom on which a gel layer is arranged and on which are also arranged upstanding walls which define a plurality of mutually adjacent, elongate rectangular compartments, said device being characterized by the fact that the vessel has at least one chamber having a plurality of rectangular compartments which are open at one short end thereof in a manner such that the rectangular gel fields located in respective compartments merge directly at the open end thereof with a further gel field extending along the short side of all said compartments. In this way it is possible to inoculate the whole of the gel layer in each chamber, including the gel fields in each compartment, with microorganisms suspended in liquid and to remove surplus inoculate in substantially the same easy manner as with the coherent gel surface in a Petri dish, thereby to save much time and, at the same time to greatly reduce the risk of infection. Moreover, a great deal of space is saved compared with the space required for determining the resistance of microorganisms using Petri-dishes.

Further, when applying antibiotics to the gel surface on which microorganisms have been sown, there is the risk of unintentionally touching said surface, whereby both the person carrying out the investigation and possibly also the equipment used may become infected. This is particularly true in the case of the disc-diffusion method, in which wrong values are obtained (too small inhibiting zones) if there is insufficient contact between the roundel and the gel surface. Consequently, each roundel must be manually pressed against the gel surface even though the application is primarily carried out with the aid of applicators. This manually effected step in the process is time consuming and, furthermore, carries the risk of infection. Consequently, it is proposed in accordance with an advantageous, further embodiment of the invention that each compartment is associated with a basin located at a considerable distance from the open end thereof, said basin being protected against contamination by microorganisms applied to the gel layer and being arranged to receive biologically active substance.

So that the invention will be more readily understood and optional features thereof made apparent, exemplary embodiments of the invention will now be described with reference to the accompanying schematic drawing, in which FIG. 1 is a perspective view of a preferred device according to the invention.

FIGS. 2 and 3 are perspective views in larger scale of parts of the device shown in FIG. 1.

FIG. 4 is a view similar to that of FIG. 3 of part of a further embodiment of the device according to the invention.

FIG. 5 is a perspective view of a part of another embodiment of the device according to the invention, and FIGS. 6, 7 and 8 illustrate three further compartment arrangements in devices according to the invention.

In the figures, identical or substantially identical elements are referenced by the same reference numerals. The device illustrated in FIGS. 1–3 for studying the effect of biologically active substances on microorganisms comprises a rectangular vessel 10 having a lid 11, which is shown removed from the vessel. The lid has a recess 12 in side walls thereof, to facilitate removal of the lid, and is, as can be seen best from FIGS. 2 and 3, somewhat larger than the vessel 10 in order to permit air or some other atmosphere to penetrate to the interior of the vessel. The lid 11 is also provided with spacers 13, in order to provide for a clearance between the lid and the upper edges of the vessel.

The vessel 10 exhibits two chambers 15 and 16 mutually separated by a partition 14. The vessel has a planar bottom 17 which is covered with a gel layer 18 of substantially uniform thickness, the gel comprising, for example, agar, agarose, acrylamide etc. Upstanding from the bottom of the vessel 10 are walls 19, 20, 21, 22 which, together with the wall 14 divide each chamber 15 and 16 into a plurality of elongate rectangular compartments which are open at one end thereof while the other end is closed, the gel fields located in respective compartments being separated laterally by the walls 22 but, at the open end of respective compartments, merge directly with a further gel field extending along the short sides of the compartments between the walls 20 and 14 and the walls 14 and 21 respectively. In this way, the whole of the gel layer 18 in each chamber 15 or 16, including the gel field in each compartment in the chamber, can be inoculated with microorganisms suspended in a liquid, for example urine, and any surplus liquid can be removed therefrom in substantially the same easy manner as the coherent gel surface in a Petri-dish, so as to considerably save time while minimizing the risk of infecting personnel.

To permit application of biologically active substances, for example different antibiotics, there are provided basins 23 (FIG. 1), which as can best be seen from FIGS. 2 and 3 are formed by holes passing through the bottom 17 of the dish, adjacent the closed end of respective compartments. Optionally, there can be arranged opposite each hole, a recess in the undersurface of the gel layer 18. To protect the basins 23 from any impurities present in the surroundings, prior to using the device 10, 11 the basins are covered with a sealing, tear-off protective strip 24 having a pull tab 25 by which the strip can be removed. As illustrated at 26 in FIG. 2, the strip 24 may also be provided with projections or pegs which fill the basins 23. Because of their location, the basins 23 are also protected, of course, from contamination from microorganisms applied to the gel layer.

When using the device 10, 11, the lid 11 is placed on the vessel 10 subsequent to the inoculating process, and the device 10, 11 is then turned upside down. After tearing off the protective strip, the biologically active substances, for example antibiotics, are applied to the basins 23. By placing the basins 23 in the bottom of the vessel, so that the biologically active substances can be applied with the lid 11 in position every risk of infecting personnel and associated equipment is eliminated. Because the vessel 10 is rectangular in shape and because the basins 23 are given a predetermined orientation relative to the vessel wall 19, the supply of biologically active substances and also the requisite evaluation of the effect of the biologically active substances on the microorganisms in question subsequent to incubation, can readily be automatized.

When applying the said active substances to the underside of the gel layer, inhibiting zones are formed in substantially the same manner as if the active substances had been applied directly to the surface sown with microorganisms. The biologically active substances can be applied in tablet or pill form, as indicated at 27 in FIG. 3; in this respect it is an advantage to give the basins a shape which is complementary to the shape of the tablets or pills. Alternatively the biologically active substances can be applied in the form of liquid solutions, with the aid of pipettes, as indicated at 28 in FIG. 3.

In the embodiment shown in FIG. 4, the biologically active substances are applied from the upper side of the vessel 10 to the basins at the closed end of respective compartments. These basins are delimited from the compartments in general by means of walls 29, which protrude into respective compartments from the side, limiting walls thereof. This embodiment also has a tear-off protective strip 24 having pegs 26 which fill the basins to prevent penetration of microorganisms thereinto when inoculating the gel surface 18.

In the embodiment shown in FIG. 5, the basins are delimited by a wall 30 which extends adjacent the closed end of respective compartments transversely of the side-limiting walls thereof, the under edge of said wall 30 being located at a distance from the vessel bottom 17 in a manner such as to form a passage, as shown at 31, from each basin 23 to its associated compartment, through which passage biologically active substances applied to the basins can diffuse to associated compartments. FIGS. 6–8 illustrate additional possible arrangements of the compartment distribution of a vessel 10 provided with two mutually separated chambers. As illustrated by the broken lines in the Figures, the walls 22 can be omitted in one of the chambers, whereby said one chamber can be used for cultivation. In this way the vessel can be used for combined cultivation and resistance determination of, for example, urine samples.

Thus, one chamber of the vessel is used for cultivation, colony counts etc., while the other chamber is used to determine directly the resistance, which saves work, space and time.

The invention is not restricted to the described and illustrated embodiments, but can be modified within the scope of the following claims. For example, the vessel may have only a single chamber or may be provided with more than two chambers which are divided into compartments open at one end thereof.

We claim:

1. A device for investigating the effect of biologically active substances against microorganisms and capable of diffusing through a gel layer having microorganisms thereon, said device comprising:
   a vessel having a bottom and a plurality of walls upstanding from the bottom to define a plurality of mutually adjacent elongate rectangular compartments and a common compartment, each of said rectangular compartments having an open end to communicate it with the common compartment;
   means defining a plurality of openings through said bottom into said rectangular compartments at positions spaced from said open ends of said compartments;
   a removeable protective strip covering said openings and having a plurality of projections positioned to be received in said openings.

* * * * *